United States Patent [19]

Wei et al.

[11] Patent Number: 5,281,535
[45] Date of Patent: Jan. 25, 1994

[54] METHOD AND APPARATUS FOR TESTING PARTS AND MATERIALS IN A CONTROLLED ENVIRONMENT SUCH AS AN ATOMIC OXYGEN ATMOSPHERE

[76] Inventors: Ronghua Wei, 1600 W. Plum, 26C, Fort Collins, Colo. 80521; Paul J. Wilbur, 1500 Teakwood Ct., Fort Collins, Colo. 80525; Samuel C. Wu, 10205 W. Exposition Ave., Lakewood, Colo. 80226

[21] Appl. No.: 906,791

[22] Filed: Jun. 30, 1992

[51] Int. Cl.$^5$ .................... G01N 17/00; G01N 19/06; G01N 3/56
[52] U.S. Cl. ........................................ 436/6; 422/53; 422/68.1; 73/9; 73/10; 73/865.6
[58] Field of Search .................. 73/7, 9-10, 73/865.6; 422/53, 63-64, 68.1, 78, 99, 67; 436/6

[56] References Cited

U.S. PATENT DOCUMENTS 3,178,928  4/1965  Howe ........................... 73/9

OTHER PUBLICATIONS

Buckley, Donald H. "Surface Effects in Adhesion, Friction, Wear, and Lubrication", *Tribology Series 5*, Elsevier Scientific Publishing Company (1981) pp. 70-73.
"Three New Accessories Extend Utility of Lubricant, Friction, and Wear Tester" Dow Corning Press Release.
Roberts, E. W. "Thin Solid Lubricant Films in Space . . ." Tribology Inst. (1990), vol. 23, (No. 2) pp. 95-104.
Fusaro, R. L. "Self-Lubricating Polymer Composites and Polymer Transfer Film . . ." Tribol. Inst (1990) vol. (23) pp. 105-122.
Arita, Masashi et al "Investigations of Tribological Characteristics of Solid Lubricants Exposed to Atomic Oxygen", Tribol Trans 35(2) pp. 374-380.
Omae, Nobuo, "Lubrication System in Ultra-High Vacuum" Tetsu to Hagane 73(10) 1297-302.
Tribological Studies of Ion-Implanted Steel Constituents Using an Oscillating Pin-On-Disk Wear Tester, Journal of Tribology, vol. 112, Jan. 1990, p. 27.
ISC-200PC Tribometer System, Implant Sciences Corporation.

*Primary Examiner*—James C. Housel
*Assistant Examiner*—Robert Carpenter
*Attorney, Agent, or Firm*—Timothy J. Martin; Dana S. Rewoldt

[57] ABSTRACT

Method and apparatus are provided for testing parts and materials in a controlled environment, especially an atomic oxygen environment. The apparatus includes a housing which has sample station located in its interior to receive a test sample. A contact element contacts a surface of the test sample, and a drive reciprocates the contact element so that the surface is subjected to wear along a wear path. At least one testing fluid is introduced and removed from the interior with the locations of introduction on removal preferably being such that the testing fluid flows across the test sample. The drive may be a carriage operated through the housing sidewall by a ferromagnetic coupling, and the sample station may be a turntable rotated by a ferromagnetic coupling. A second sample station may be included so that different wear path configurations are possible. The method includes the steps of placing a test sample on a sample support station, contacting the test sample with a contact element, isolating the interior of the housing from the ambient environment, introducing and removing at least one testing fluid at locations such that the testing fluid flows across the test sample, reciprocally moving the contact element on the test sample and measuring an amount of wear after a selected interval of time. Preferably, the test sample is rotated during reciprocation of the contact element. Temperature and pressure may be monitored and controlled.

35 Claims, 6 Drawing Sheets

METHOD AND APPARATUS FOR TESTING PARTS AND MATERIALS IN A CONTROLLED ENVIRONMENT SUCH AS AN ATOMIC OXYGEN ATMOSPHERE

FIELD OF THE INVENTION

The present invention is directed to the field of testing materials and parts for wear and friction characteristics, which field is commonly known as tribology. Particularly the invention concerns a method and apparatus for the testing of samples of selected materials having compositions that are to be used in the fabrication of mechanical parts under environmental conditions controlled to simulate an operative environment. The invention concerns testing at an accelerated rate to determine wear rate and coefficient of friction. Even more specifically, the present invention provides a method and apparatus for testing materials and parts in a controlled atomic oxygen atmosphere.

BACKGROUND OF THE INVENTION

The field of tribology concerns the study of friction and wear between material surfaces in contact and under relative sliding motion. Thus, the field of tribology involves measurement and calculation of such parameters as friction and wear rate of materials such as used in the construction of mechanical parts. Knowledge of these parameters is useful for the study of the behavior of the same or different materials in moving contact in order to evaluate materials to be used in the construction of mechanical parts and to estimate the potential for failure of those parts over time.

Tribotesting apparatus has previously been developed to test the wear characteristics of material samples. The traditional tribotester is referred to the "pin-on-disk" tester wherein a sample of material is placed on a turntable that may be rotatably driven. A contact element may be subjected to different loading forces so that it bears normally downwardly on the sample of material and, as the sample of material rotates on the turntable, a single wear band is traced in a circle around the material sample. The point of the contact element may be formed of the same material as the sample or a different material, as desired. An added feature of rotating the sample while radially oscillating the contact element may be employed by a tribotester thereby to cause the contact element to trace a spiral line across the surface of the sample. Accordingly, a wear path in the shape of a race track would be formed on the sample with this race track having a width equal to the radial distance over which the contact element is reciprocated. In the abovedescribed cases, the tribotesting apparatus was designed to operate under normal ambient environment conditions.

Knowing the wear characteristics of materials under normal ambient conditions is quite useful since many applications of materials are in situations of normal ambient atmosphere such as is found on the surface of the earth. However, an increasing number of applications are in conditions other than the normal ambient environmental conditions. One such example would be found in the semi-conductor industry wherein a substantial portion of processing is done in atmospheres that are rich in corrosive gases.

Another area where conditions are significantly different from earth surface normal is in the aeronautics and space industry. For example, in high altitude and earth orbit that the atmosphere is greatly rarefied, and a significant problem manifests in the presence of atomic oxygen, a highly corrosive gas that which readily attacks many lubricious materials. Thus, the surfaces of mechanical parts which are designed for relative movement with reduced friction rapidly become degraded and may fail. The search for materials resistive to atomic oxygen goes on in an effort to locate materials less susceptible to failure due to the corrosive nature of atomic oxygen in these environments. Other examples in the space industry, of course, are the atmospheres of different planets.

Yet another example of an environment of increasing interest is the undersea environment wherein the corrosive action of salt water may also act to degrade materials employed in underwater equipment. Propeller shafts are known to fail in their bearings as a result of the degradation from the corrosive nature of sea water; likewise, oil drilling and undersea mining applications employ machines susceptible to such degradation.

Accordingly, a need exists for methods and apparatus to test the wear characteristics of materials in environments different than the ambient environment at the surface of the earth. The need exists for such testing equipment which may be used to test materials in a fluid environment that may be in the liquid phase or gaseous phase. The present invention addresses these needs.

SUMMARY OF THE INVENTION

It is an object of the present invention to provide a new and useful method and apparatus for the testing of materials in a controlled environment that is simulated to be either of a type corresponding to a specific altered industrial environment, of a type that naturally exists, but not at earth's surface, or of a type corresponding to an undersea environment.

A further object of the present invention is to provide a new and useful method and apparatus which can test the wear characteristics of materials which are subjected to a flowing environment.

Another object of the present invention is to provide a new and useful method and apparatus for testing of materials subjected to an atomic oxygen environment such as found at high altitude and earth orbit environments.

Still a further object of the present invention is to provide an improved tribotesting structure having alternative test stations allowing testing by way of either a linear elongated wear path, a circular wear path or a circular "racetrack" wear path.

According to the present invention, then, a method and apparatus is described wherein tests may be performed on sample materials in a controlled, test environment. Generally, the apparatus according to this invention includes a housing that defines an enclosure having an interior in which may be created the controlled test environment. The housing has surrounding wall portions at least one of which may be removed to allow access in the interior thereof and which may be secured to the housing to isolate the interior. A first sample station is disposed in the interior of the housing, and a contact element is also disposed in the interior of the housing and is operative in an active state to contact a surface of the sample with a selected contact force when the sample is supported on the sample station. A drive system is provided for moving the contact element relative to the surface at a selected rate in order to subject the surface to wear along a wear path. A system for introducing the test fluid into the interior of the housing when it is in a closed state is provided in order to create a test fluid environment, and a system for removing the test fluid from the interior of the housing when in the closed state concurrently with the introduction of the test fluid is also provided so that the test fluid flows around the sample and contact element.

In this apparatus, the test fluid may be a gaseous material and, it is a specific embodiment of the invention that the test gas be atomic oxygen. Here, the atomic oxygen is introduced into the interior of the test chamber by disposing a plasma generator actually in the interior of the housing proximate to the sample to be tested in order to decompose molecular oxygen into atomic oxygen. Where the test fluid is a gas the present invention includes sensors to measure pressure. When using either a liquid or a gas as the test fluid, sensors may be provided to monitor temperature and, to this end, heating and cooling units may be provided to maintain the test fluid at a pre-selected temperature.

A plurality of test fluids may be introduced into the interior of the housing from a plurality of fluid sources or, as in the case of atomic oxygen, by generators disposed in the interior of the housing. In either event, where a plurality of test fluids is utilized, it is preferred to include a sensor for monitoring the composition of the resulting test fluid environment and a control system provided for independently adjusting the proportions of the components to maintain a selected ratio.

In the preferred embodiment, the testing apparatus includes a generally square-shaped housing having a flat bottom wall and a removable top wall which is pivotally secured to the sidewall so that it may be raised and lowered to seal the interior of the housing. A movable carriage is disposed in the interior of the housing and is mounted for reciprocal movement with respect to the bottom wall. A first drive system is drivably interconnected to the movable carriage and includes a first motor disposed exteriorly of the housing and a drive assembly disposed interiorly of the housing with the motor and first drive assembly being interconnected by means of a first ferromagnetic coupling so that the first motor linearly moves the carriage reciprocally at a selected rate of travel between first and second limits. The first sample station is in the form of a turntable disposed in the interior of the housing and spaced from the carriage along the bottom wall. A second drive system operates to rotatably drive the turntable and includes a second motor disposed exteriorly of the housing and a second drive assembly disposed interiorly of the housing and interconnected through the bottom wall by means of a second ferromagnetic coupling. Thus, the second motor may rotatably drive the turntable at a selected rate of rotation. The contact element is disposed on a second end of a support arm which has a first end mounted for movement with the carriage is positionable in an first orientation wherein the second arm is proximate to the turntable. The travel limits of the carriage are adjustable by means of first and second sensors such as optical interrupters, which are adapted to sense the position of the carriage respectively at the first and second limits and generate a signal to reverse the direction of the carriage respectively when it reaches the first and second limits. Both the rate of travel of the carriage and the rate of rotation of the turntable may be varied. A strain gauge may be associated with the support arm to measure strain on the contact element during wear testing. Furthermore, it is preferred to provide structure that allows variance of the magnitude of the contact force. A cuing structure may be provided to raise and lower the contact element off of and onto the sample and, to this end, the support arm is pivotally secured to the carriage. Finally, if desired, a second sample station in the form of a stationary block may be disposed in the interior of the housing at a selected distance from the carriage to define a second sample station. Where the second sample station is provided, the support arm may be positionable in a second orientation wherein the second arm end is proximate to the stationary block.

According to the method of the present invention a process for testing a sample of material in a controlled environment includes the step of providing a closed environment housing having an interior that may be isolated from the ambient environment and which has disposed therein a sample support station adapted to support a sample thereon, and a sample may be placed on the support station. This method includes the step of isolating the interior of the closed environment housing from the ambient environment and introducing a test fluid into the interior of the housing whereby the test fluid flows around the sample and contact element. The method includes the step of contacting a surface of the sample with a contact element at a selected contact force while the sample is supported on the sample support station. The general method finally includes the step of reciprocally removing the contact element relative to the surface of the sample at a selected rate when the contact element is in contact therewith whereby the surfaces subjected to wear along a wear path.

A more specific method may include the step of rotating the sample of material while reciprocally moving the contact arm in a radial direction respective thereto. This method may also include the step of monitoring the temperature of the test fluid environment and controlling the temperature so that a selected temperature is maintained. Likewise, the method may include the step of monitoring the pressure of the test fluid environment and adjusting the pressure to maintain a pre-selected value. Further, where a plurality of test fluids are provided, the method may include the step of monitoring the composition of the test fluid environment and adjusting the proportion of the composition to a selected ratio. Further, the specific process employed in the present invention includes the step of reducing the pressure of the interior of the closed environment housing below ambient pressure and introducing atomic oxygen at a location proximate to the sample. Here, the composition of atomic oxygen may be monitored and adjusted to maintain a pre-selected ratio of atomic oxygen in the test fluid environment.

These and other objects of the present invention will become more readily appreciated and understood from a consideration of the following detailed description of the preferred embodiment when taken together with the accompanying drawings, in which:

DETAILED DESCRIPTION OF THE EXEMPLARY EMBODIMENTS

The present invention is directed to a process and apparatus for testing materials and parts for wear characteristics. The present invention specifically concerns the measurement of wear parameters of one material against itself or a different material. These parameters include wear rate and the coefficient of friction. While tribology testing equipment has been developed in the past, the present invention discloses improved tribotester structure, the use of tribotesting equipment in an altered and controlled environment, and, specifically, structure to permit the testing of materials in environments containing increased percentages of atomic oxygen. Thus, the present invention is useful not only for testing materials at normal ambient conditions experienced at the surface of the earth, but in different environments which may be encountered in manufacturing process, at high altitude or sub-space, in relative vacuum, and even on other planets.

Figure 1:
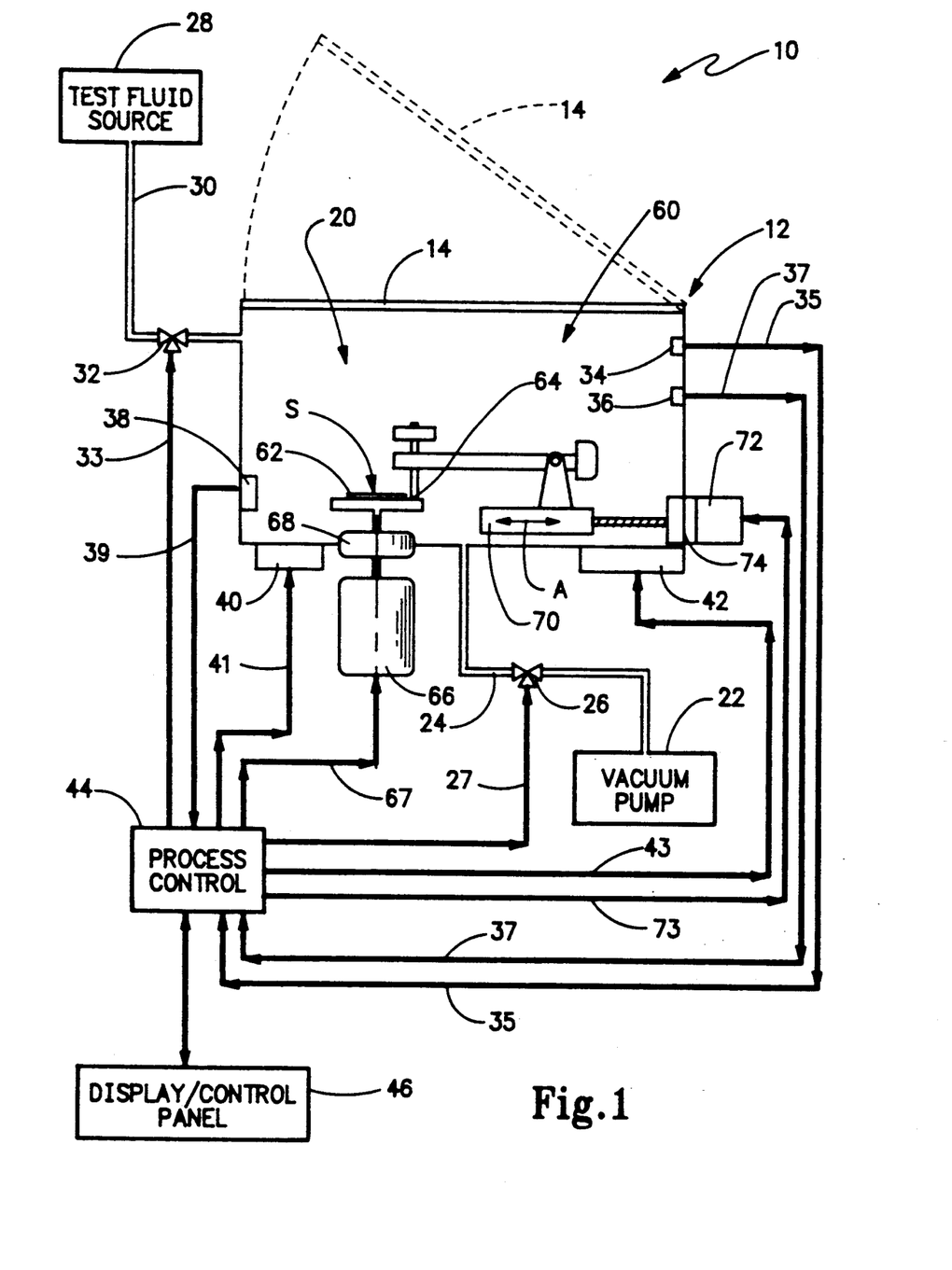
FIG. 1 is a diagrammatic view of a controlled environment testing apparatus according to a first exemplary embodiment of the present invention.
Figure 2:
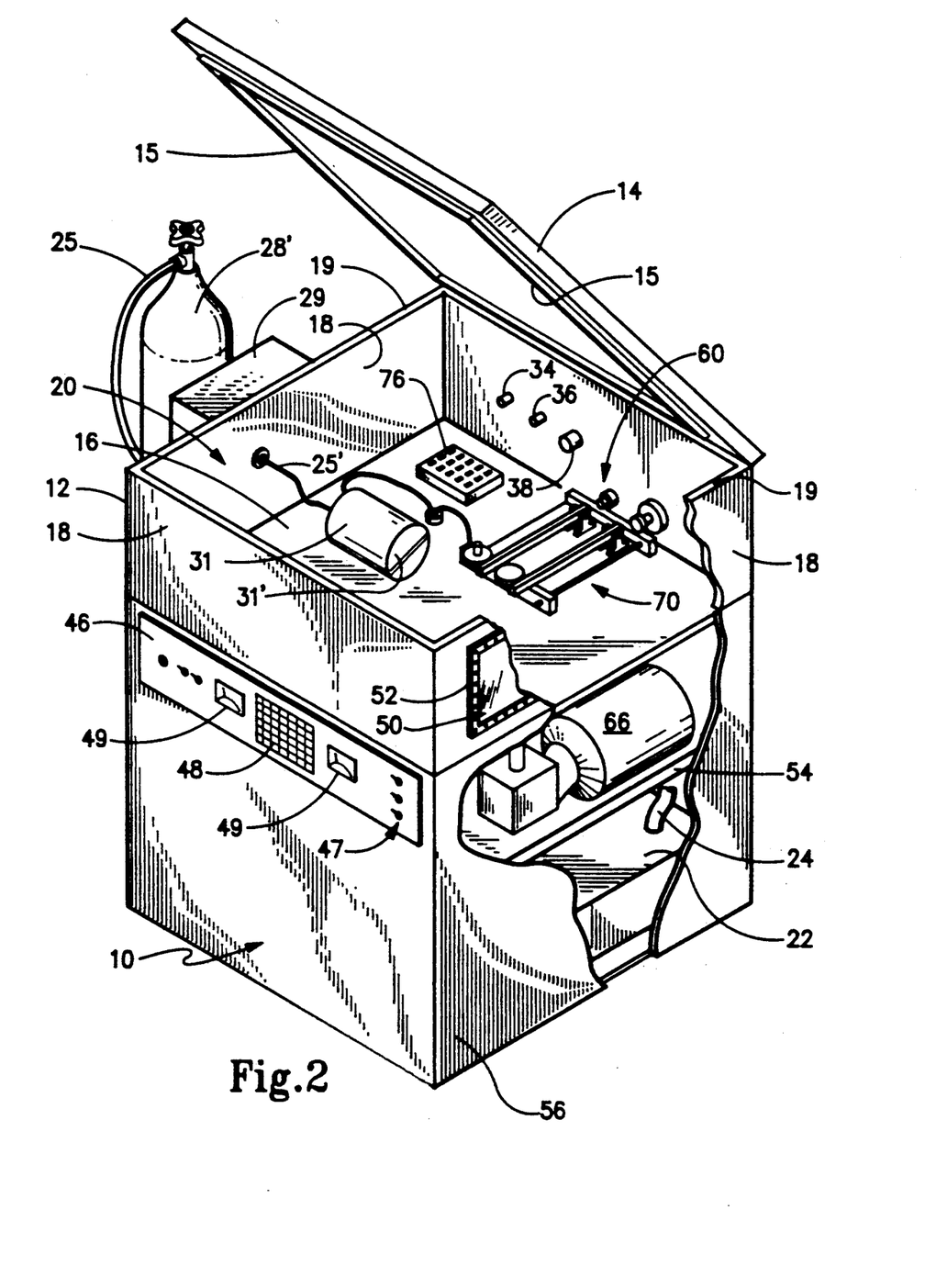
FIG. 2 is a perspective view, partially cut-away, showing a controlled environment testing apparatus according to the present invention with the test chamber in an open state.

Accordingly, and with reference to FIGS. 1 and 2, it may be seen that testing apparatus 10 according to a first exemplary embodiment of the present invention broadly includes a closable housing 12 having a top wall or lid 14 that is movable between a closed position shown in FIG. 1 and an open position shown in FIG. 2 (and in FIG. 1 in phantom). Housing 12 includes a bottom wall 16 and opposite lid 14 and a surrounding sidewall 18 so that, when lid 14 is in the closed position, interior 20 of housing 12 is relatively sealed against the exterior and the environment. To this end, lid 14 is provided with a suitable gasket 15 extending around is periphery, and gasket 15 engages and seals against upper rim 19 of sidewall 18 when lid 14 is closed.

A vacuum pump 22 is in fluid communication with the interior 20 of housing 12 by way of conduit 24 and valve 26. A test fluid may be introduced into the interior 20 of housing 12 or, alternatively, may be created within the interior of housing 12, as is shown in FIG. 1, a test fluid source 28 is in fluid communication with interior 20 of housing 12 through a conduit 30 and a valve 32. In FIG. 2, the test fluid source 28 includes a tank of oxygen 28' in fluid communication via hose 25 with an asher plasma generator 29. Asher generator 29 is, in turn, in fluid and electrical communication with its antenna 31 by way of conduit 25' so that outlet slit 31' of antenna 31 is proximate to the first sample station, described more thoroughly below. Asher generator 29 operates to convert the molecular oxygen from tank 28' into atomic oxygen at antenna 31 which atomic oxygen is ejected through outlet 31'. In either event, the pressure and temperature of the controlled test environment in interior 20 is monitored by a pressure sensor 34 and a temperature sensor 36 which are connected through input wires 35 and 37, respectively, to a process control unit 44. Process control unit 44 may be any suitable digital control device, such as a programmed personal computer or the like, as is known in the art. Likewise, the composition of the test fluid environment in the interior 20 may be monitored by sensor 38 which is connected to process control unit 44 by input wire 39.

As diagrammed in FIG. 1, the temperature of the test environment in interior 20 of housing 12 may be adjusted either by heating unit 40 o cooling unit 42 which may be controlled by process control unit 44 over signals sent on control wires 41 and 43, respectively. Process control unit 44 likewise may control the opening and closing of valves 26 and 32 so that a static test environment may be created in interior 20. Alternatively, process control unit 44 can adjust the relative flow rates through valves 26 and 32 in order to create a dynamic test fluid environment which moves through interior 20. Process control unit 44 controls valves 26 and 32, respectively, by way of signals on control wires 27 and 33. Here, valves 26 and 32 should be automated as is well known in the art. Alternatively, valves 26, 32 can be manually operated. As is shown in FIG. 2, process control unit 44 has a control/display unit 46 provided with control switches, such as switches 47, input device 48 and meters such as meters 49, as desired for the particular configuration of testing apparatus constructed and according to the type of processing unit 44. Furthermore, as is shown in FIG. 2, a portion of sidewall 18 may be provided with a view port 50 which is mounted over an opening in sidewall 18 by means of a sealed bracket assembly 52. View port 50 should be constructed of a transparent material of a type resistive to corrosive gases or which is inexpensive to replace or repair.

Figure 3:
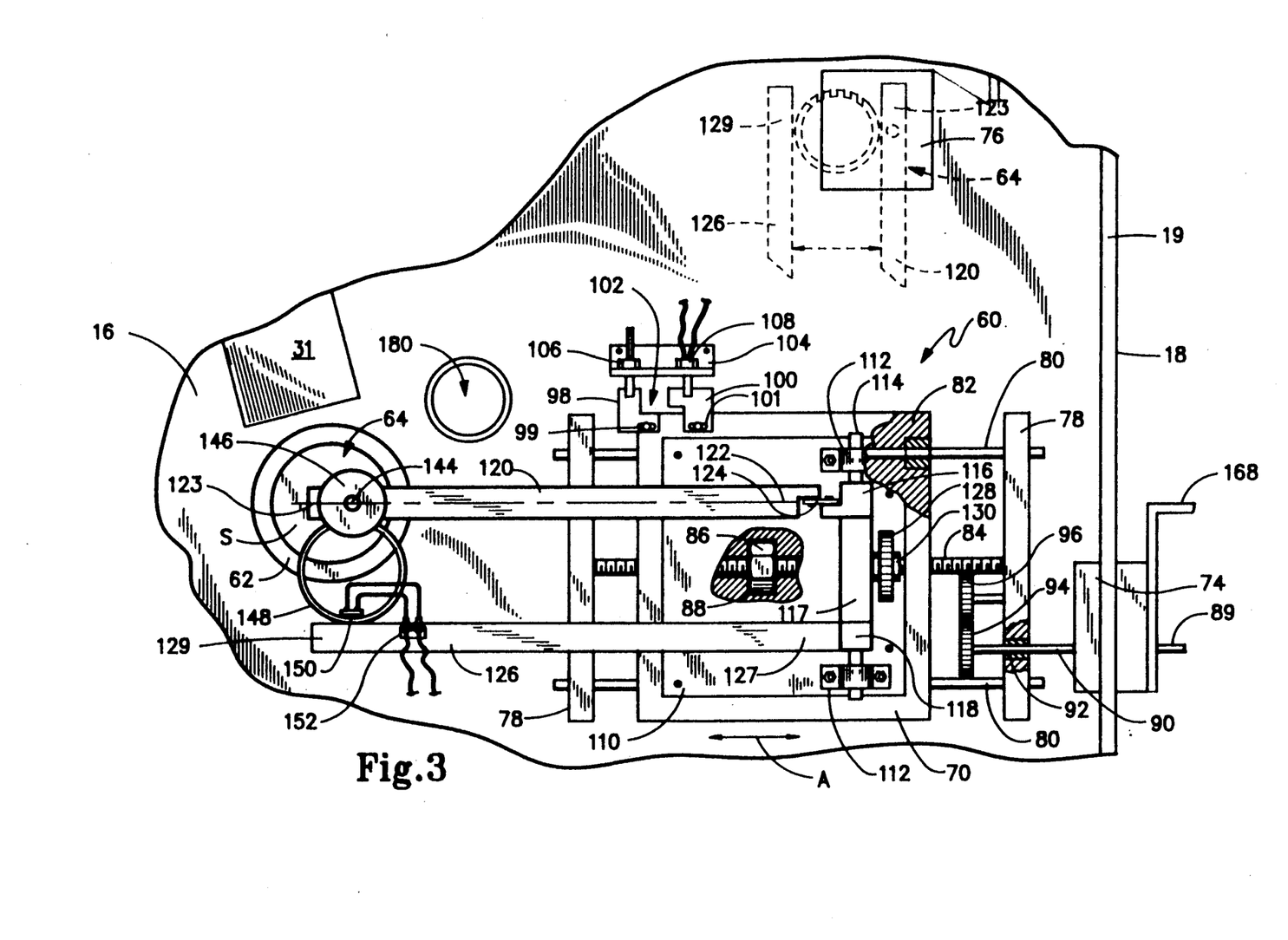
FIG. 3 is a top plan view of the tribotester assembly shown in FIG. 2.

Improved tribotesting apparatus 60 is mounted in interior 20 of housing 12 and, as is shown in FIGS. 1 and 3, includes a first sample station that is adapted to support a sample "" thereon and a contact element 64 that is operative in use to contact the surface of sample "S" placed on sample station. As described more thoroughly below, the first sample station is in the form of a turntable 62 which is rotatably driven by a variable speed motor 66 acting through ferromagnetic coupler 68. Motor 66 is controlled by process control unit 44 by means of control wire 67. Contact element 64 may be reciprocally driven in the direction of arrow "A" by means of a moving carriage 70 that is driven by reversible DC motor 72 acting through ferromagnetic coupling 74. Motor 72, in turn, may be controlled by process control unit 44 over control wire 73. Also, as is shown in FIG. 2, a second sample station may be provided in the form of a stationary block 76 mounted to bottom wall 16 of housing 12. As described below, stationary block 76 is spaced in equal distance from moving carriage 70 as is turntable 62 so that it provides an alternate mounting station for a sample "S".

Figure 4:
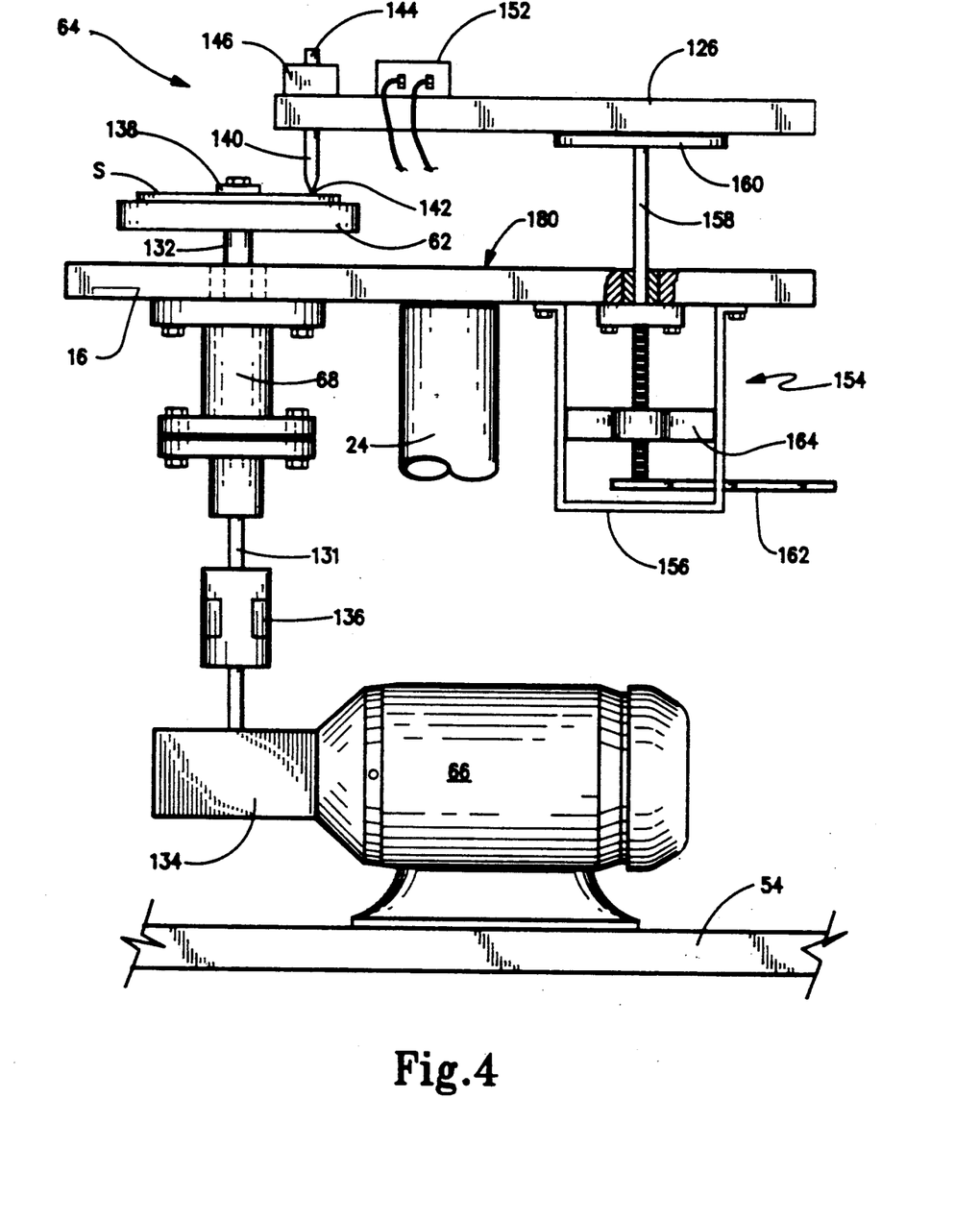
FIG. 4 is a side view in elevation, in partial cross-section, showing the contact pin, turntable and cuing structure of the tribotester apparatus of FIG. 3.
Figure 5:
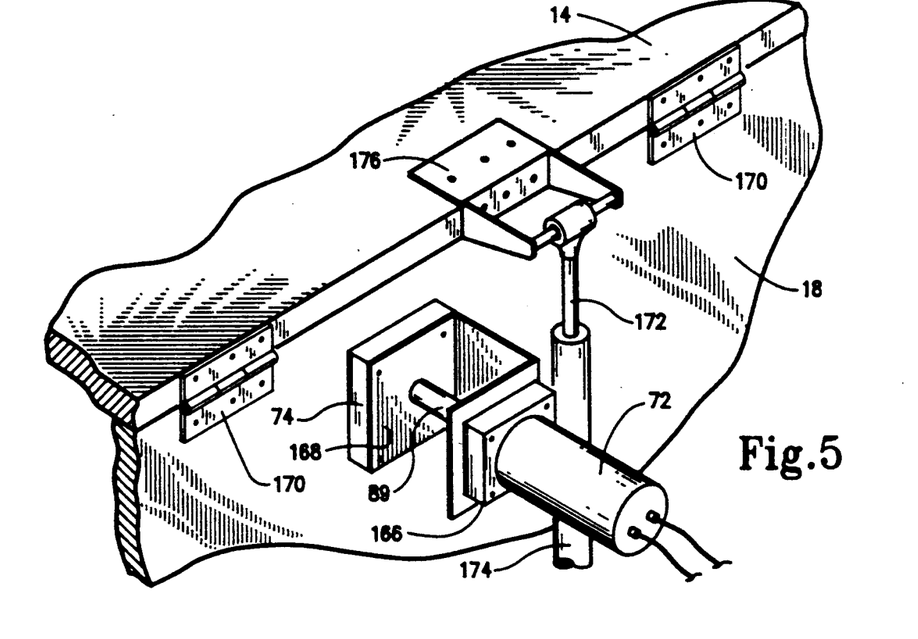
FIG. 5 is a perspective view of the linear motion drive and the lid assembly for the controlled environment testing apparatus of FIGS. 1-4.

The improved tribotesting apparatus 60 is shown in greater detail in FIGS. 3-5. In FIG. 3, it may be seen that moving carriage 70 is mounted between a pair of parallel rigid mounting blocks 78 by means of a pair of parallel Thompson rods 80. Each of Thompson rods 80 is provided with matched bearings, such as bearing 82 which are mounted within carriage 70 at each corner thereof. A threaded rod 84 is mounted equidistantly between Thompson rods 80 and parallel thereto and is rotatably journaled between mounting blocks 78. Threaded rod 84 threadably receives a nut 86 that is mounted in cavity 88 centrally of carriage 70. In operation, as threaded rod 84 is rotated, nut 86, which is locked into position with respect to carriage 70, is forced to advance longitudinally of rod 84 and, correspondingly, carriage 70 is driven in the direction of arrow "A". In order to accomplish this motion, output shaft 90 of ferromagnetic coupling 74 is rotatably supported by bearing 92 in mounting block 78 and terminates in a drive gear 94 which correspondingly rotates with shaft 90. Transfer gear 96 is rotatably journaled to mounting block 78 and is driven by drive gear 94. Transfer gear 96, in turn, is rotatably threaded on rod 84. Output shaft 90 is, driven through ferromagnetic coupling 74 by means of input shaft 89 rotatably driven by DC motor 72 as described below with respect to FIG. 5.

A pair of slotted wings 98 and 100 are adjustably mounted along one edge of carriage 70 parallel to drive rod 84 and respectively includes adjustment slots 99 and 101 so that a relative space 102 therebetween may be adjustable in width. Bracket 104 is mounted to bottom wall 16 and supports a pair of optical isolators 106 and 108 which detect space 102 thereby to generate a signal operative to reverse the direction of DC motor 72. Accordingly, it should be understood that optical isolators 106, 108 along with wings 98, 100 define the extrema or limit locations for the reciprocal travel of carriage 70.

A removable plate 110 is mounted on the upper surface of moving carriage 70 and may be considered part thereof. Plate 110, in turn, mounts a pair of opposed pillow blocks 112 between which an axle 114 is pivotally journaled. A support arm 120 has a first end 122 which is mounted to axle 114 by means of a length of spring steel 124 affixed to rigid block 116 that is rigidly mounted to axle 114. Contact element 64 is located at a second end 123 of support arm 120 opposite first end 122. Similarly, a rigid arm 126 has a first end 127 that is rigidly affixed to axle 114 by mean of block 118 that is in turn rigidly mounted on axle 114. Sleeve 117 is also affixed to axle 114 and extends between blocks 116 and 118; sleeve 117 has a shaft 130 that extends radially of sleeve 117, and shaft 130 threadably receives a counterweight 128. Rigid arm 126 terminates in a second end 129 opposite first end 127 so that support arm 120 and rigid arm 126 are substantially parallel to one another.

Since axle 114 is rotatably journaled between pillow blocks 112 mounting arm 120 and rigid arm 126 may pivot together from an orientation substantially parallel to bottom wall 16 to an orientation at an acute thereto. This allows contact element 64 to move into and out of an active state wherein a contact force is applied to a material sample "S" located on turntable 62. It should also be appreciated that, since plate 110 is removably mounted on carriage 70, it may be rotated at 90° into the orientation shown in phantom in FIG. 3 so that ends 123 and 129, respectively, of support arm 120 and rigid arm 126 proximate to stationary block 76, which forms the second sample station, so that contact element 64 may address a sample placed on stationary block 76. For this reason, stationary block 76 is spaced or distanced from carriage 70 that is substantially equal to the distance between carriage 70 and turntable 62.

With reference to FIGS. 3 and 4, it may now be appreciated that turntable 62 may be rotatably driven by means of output shaft 132 of ferromagnetic coupling 68. To this end, ferromagnetic coupling 68 is mounted through bottom wall 16 of housing 12 and has an input shaft 131 which is driven by variable speed motor 66 acting through gear box 134 and coupling 136. Motor 66 is supported on suitable frame member 54 housed in enclosure 56 (FIG. 2).

As shown again with reference to FIGS. 3 and 4, a sample "S" of material may be mounted by fastener 138 onto an upper surface of turntable 62 so that it may be addressed by contact element 64. Contact element 64 includes a contact pin 140 which terminates in a tip 142 that releasably mounts a contact material to be applied to the surface of sample "S". This material may be the same material as sample "S" or a different material, as desired for a particular test. Pin element 140 has an upper shank 144 which may receive calibrated weights, such as weight 146 in order that a selected contact force may be applied to the surface of sample "S". To this end also, counterweight 128 helps counterbalance this assembly. Further, in order to measure friction between the tip of pin 140 and the surface of sample "S", a strain gauge in the form of compression ring 148 is mounted between end portions 123 and 129 of support arm 120 and rigid arm 126, respectively. Measurement of the strain on contact pin 140 allows measurement of a drag friction force of contact pin 140 in the direction of a tangential vector when sample "S" is rotated. Suitable sensors 150 are provided to measure the strain on compression ring 148 and electrical contact is made to sensors 150 by means of harness 152.

A cuing system is provided so that support arm 120 and rigid arm 126 may be pivoted upwardly away from bottom wall 116 when housing 12 is in the closed position. Thus, as is shown in FIG. 4, cuing system 154 includes a bracket 156 which rotatably supports a threaded shaft 158 that terminates in a support plate 160 that bears against an underside of rigid arm 126. Shaft 158 may be rotated by means of handle 162 so that plate 160 is raised and lowered due to interaction with threaded nut 164 mounted to bracket 156. This in turn raises contact pin 140 off of and on to the surface of sample "S".

With reference to FIG. 5, it may be seen that reversing DC motor 72 rotatably drives input shaft 89 of ferromagnetic coupler 74 by way of a gear box 166. Gear box 166 and motor 72 are accordingly mounted to sidewall 18 of housing 12 by means of ferromagnetic coupler 74 and a U-shaped bracket 168. Furthermore, as may be more fully appreciated with reference to FIG. 5, top wall or lid 14 may be pivotally mounted to sidewall 18 by means of hinges, such as hinges 170, so that lid 14 may be pivoted between the closed and open positions. To this end, a drive rod 172 is driven by means of cylinder 174 which may be a screw drive cylinder, hydraulic cylinder or the like, as is known in the art. Extension and retraction of rod 172 acts on lid 14 by way of a crank bracket 176 secured to lid 14.

With reference again to FIGS. 1-4, it may now be seen that a port 180 is formed through bottom wall 16 of housing 12 and provides an outlet for interior 20. Conduit 24, in the form of a vacuum hose, may extend from outlet 180 to vacuum pump 22 so that vacuum pump 22 may evacuate interior 20 when lid 14 is in the closed position. Once evacuated, a valve, such as valve 26, may be closed and the test fluid environment may be created in the interior of housing 12 by introducing the test fluid therein. This can take place from an exterior test fluid source, such as source 28, shown in FIG. 1, or by way of creating the test fluid at a location proximate to sample "S". For example, in the exemplary embodiment shown in FIGS. 2-5, a plasma generator 29 is placed proximate to turntable 62 and acts to create atomic oxygen. Antenna 31 has a slot 31' through which atomic oxygen may escape. Where an external source of fluid is provided, it should also be appreciated that process control unit 44 can continuously operate vacuum pump 22 and control the relative openings of valve 26 and 32 so that a dynamic flowing environment of test fluid may be presented to sample "S" during testing.

Figure 6A:
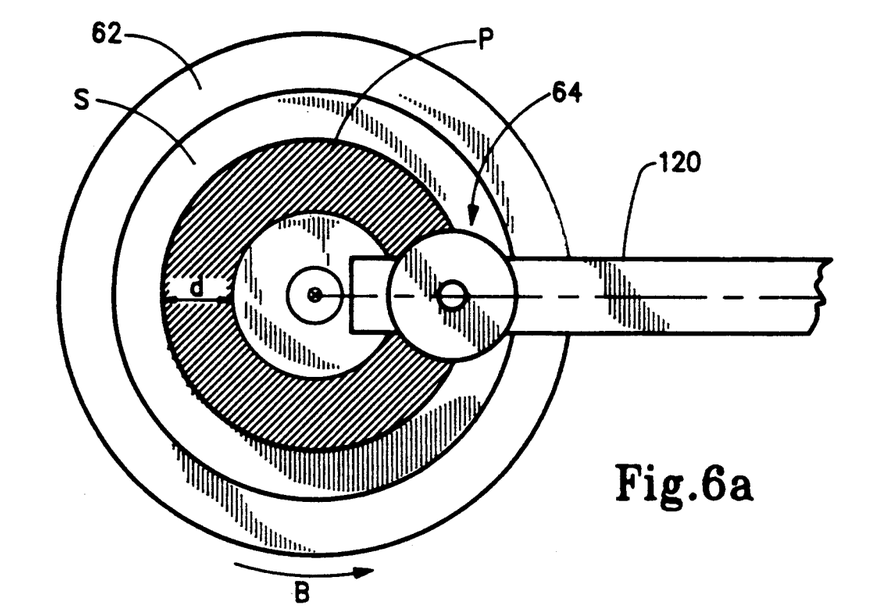
FIG. 6(a) and 6(b) are top plan views showing the wear paths on samples placed respectively on the first and second sample stations shown in FIG. 3.
Figure 6B:
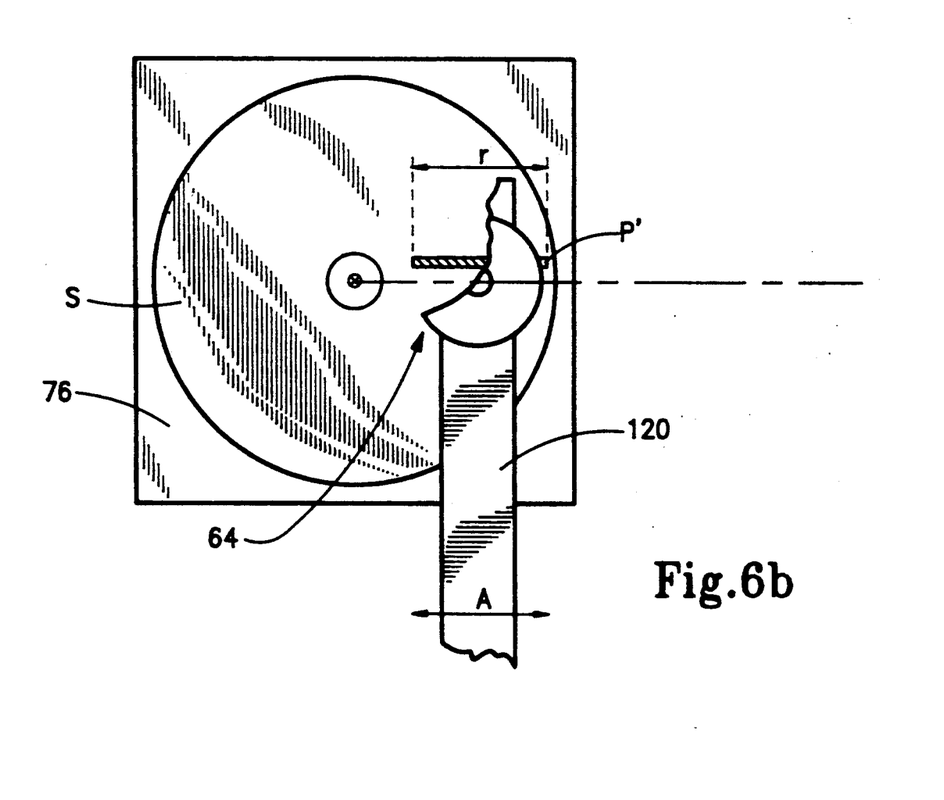

As noted above, a sample may be placed on either turntable 62 or stationary block 76. With reference to FIG. 6(a) it may be appreciated that, when sample "S" is rotated on turntable 62 in the direction of arrow "B", contemporaneous reciprocal movement of contact element 64 a radial distance "r" causes a spiral track to be inscribed on sample "S". Over time, the spiral tracking of contact element 64 creates a race track shaped (i.e., an annular band) wear path "P" having a width "d" equal to radial distance "r". However, when a sample "S" is place on stationary block 76, as depicted in FIG. 6(b) reciprocal movement of contact element 64 the distance "r" results in wear path P' in the shape of an elongate band.

Figure 7:
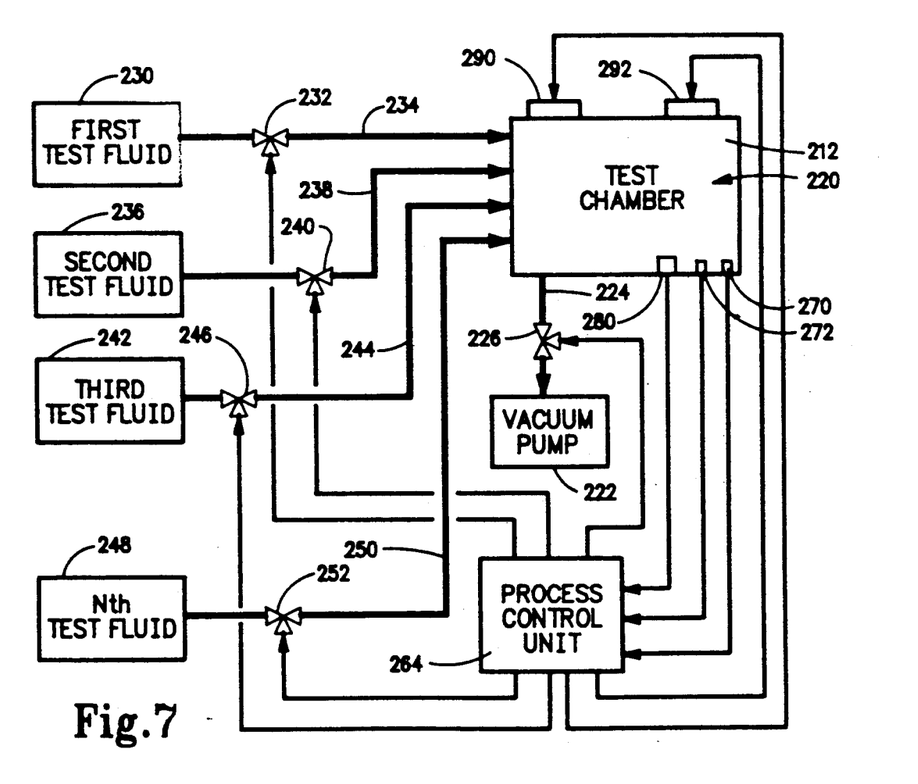
FIG. 7 is a diagrammatic view showing an alternate embodiment of the present system.

With reference to FIG. 7, it may be appreciated that any number of sources of test fluids may be provided for test chamber 212 which corresponds to housing 12, above, and which has an interior 220. For example, as is shown in this figure, first test fluid 230 is connected by way of conduit 234 into test chamber 212 and the flow therethrough is controlled by valve 232. Second test fluid 236 flows through conduit 238, and the flow of this fluid is controlled by valve 240. Third test fluid 242 flows through conduit 244 with this flow being controlled by valve 246, and an Nth test fluid 248 flows through conduit 250 that is controlled by valve 252. Valves 232, 240, 246 and 252 are controlled by means of process control unit 264. Likewise, vacuum pump 222 may evacuate test chamber 212 by way of conduit 224 acting through valve 226. Valve 226 is likewise controlled by process control unit 264.

Test conditions in interior 220 of test chamber 212 are monitored by means of temperature sensor 270, pressure sensor 272 and composition sensor 280 which provide inputs to process control unit 264. Process control unit 264 may operate heating unit 290 or cooling unit 292 to control the temperature within test chamber 212, and by operation of the various valves 232, 240, 246, 252 and 226, may control both the pressure and composition of the test fluid environment in the interior 220 of test chamber 212. Thus, it should be fully understood by the skilled artisan that the environment in test chamber 212 may be a static environment of a desired configuration or a dynamic environment of a desired configuration.

According to the foregoing description, it should now be appreciated that the apparatus described allows for a new and useful testing methodology comprised of a series of processing steps. This method may include the first step of providing a closed environment housing having an interior that may be isolated from the ambient environment and which has disposed therein a sample support station adapted to support a sample of material thereon. The method includes the step of isolating the interior of the closed environment housing from the ambient environment and introducing a test fluid into the interior of the housing whereby the test fluid flows around the sample and contact element. The test fluid may be removed from the interior of the housing concurrently with the introduction of the test fluid whereby the test fluid flows around the sample and contact element. The method includes the step of contacting a surface of the sample placed on the sample support station with a contact element at a selected contact force. Finally, this method includes the step of reciprocally moving of the contact element relative to the surface of a sample at a selected range when the contact element is in contact therewith whereby the surface of the sample is subjected to wear along a wear path.

The method may also include the step of rotating the sample of material contemporaneously while reciprocally moving the contact element in a radial direction respective thereto so that the wear path is in the form of a race track having a width equal to the distance of reciprocal motion. The method may also include the step of monitoring the temperature of the test fluid environment and controlling the temperature so that a selected temperature is maintained. Likewise, the method may include the step of monitoring the pressure of the test fluid environment and adjusting the pressure to maintain a pre-selected pressure. Further, the method includes the step of providing a plurality of test fluids and the monitoring of the composition of the test fluid environment and adjusting the proportion of the composition to a selected ratio of said test fluids. Furthermore, this method includes the step of reducing the pressure of the interior of the closed environment housing below ambient pressure and introducing atomic oxygen at a location proximate to the test sample. Here, the ratio of atomic oxygen in the test fluid environment may be monitored and adjusted to maintain a pre-selected percentage.

Accordingly, the present invention has been described with some degree of particularity directed to the preferred embodiment of the present invention. It should be appreciated, though, that the present invention is defined by the following claims construed in light of the prior art so that modifications or changes may be made to the preferred embodiment of the present invention without departing from the inventive concepts contained herein.

We claim:

1. An apparatus for testing a test sample in the presence of a selected testing fluid environment, comprising:
   (a) a housing including surrounding wall portions that enclose an interior, at least one of said wall portions being removable from said housing whereby said housing may be opened to allow access to the interior thereof and being securable to said housing whereby said housing may be closed to isolate the interior thereof;
   (b) a first sample station disposed in the interior of said housing and adapted to support a test sample thereon;
   (c) a contact element disposed in the interior of said housing and operative in an active state to contact a surface of said test sample with a selected contact force when said test sample is supported on said first sample station;
   (d) means for moving said contact element relative to said surface at a selected rate when said contact element is in the active state whereby said surface is subjected to wear along a wear path;
   (e) a source of testing fluid;

(f) means for introducing the testing fluid into the interior of said housing at a first location when in a closed state; and (g) means for removing the testing fluid from the interior of said housing at a second location when in the closed state concurrently with the introduction of said testing fluid, the first and second locations being oriented with respect to said sample station such that said testing fluid flows across said test sample and said contact element whereby said test sample and said contact element are subjected to a selected testing fluid environment when in the active state.

2. Apparatus according to claim 1 wherein said testing fluid is a gas.

3. Apparatus according to claim 2 wherein said gas is atomic oxygen.

4. Apparatus according to claim 2 further comprising a pressure sensor operative to sense gas pressure in the interior of said housing and including process control means for monitoring and controlling said gas pressure.

5. Apparatus according to claim 1 further comprising a plurality of sources of different testing fluids, means for respectively introducing each of said testing fluids into the interior of said housing when in the closed state as the selected testing fluid environment, means for monitoring the composition of said testing fluid environment, and process control means for independently adjusting the introduction of each of said testing fluids whereby a selected composition of the testing fluid environment is maintained.

6. Apparatus according to claim 1 further comprising a temperature sensor operative to sense the temperature of said testing fluid environment and process control means for monitoring said temperature.

7. Apparatus according to claim 6 further comprising means for regulating the temperature of said testing fluid environment, said process control means operative to control said means for regulating said temperature.

8. Apparatus according to claim 1 further comprising means for adjusting said contact force.

9. Apparatus according to claim 1 wherein said first sample station is rotatably mounted with respect to said housing and further comprising a rotatable drive for rotating said sample station, said means for moving said contact element operative to move said contact element radially of said sample station whereby said contact element travels in a spiral path with respect to said first sample station so that said wear path is configured as an annular band.

10. Apparatus according to claim 9 further comprising a second sample station disposed in the interior of said housing and spaced from said first sample station, said second ample station being stationarily mounted with respect to said housing station, said contact element being positionable within said housing to independently address a select one of said first and second sample stations, said means for moving said contact element operative to move said contact element when positioned adjacent to said second sample station so that said wear path is configured as an elongate band.

11. An apparatus for testing a test sample in the presence of a selected testing fluid containing atomic oxygen, comprising:

(a) a housing including surrounding wall portions that enclose an interior, at least one of said wall portions being removable from said housing whereby said housing may be opened to allow access to the interior thereof and being securable to said housing whereby said housing may be closed to isolate the interior thereof;

(b) a sample station disposed in the interior of said housing and adapted to support a test sample thereon;

(c) a contact element disposed in the interior of said housing and operative in an active state to contact a surface of said test sample with a selected contact force when said test sample is supported on said sample station;

(d) means for moving said contact element relative to said surface at a selected rate when said contact element is in the active state whereby said surface is subjected to wear along a wear path;

(e) means for introducing atomic oxygen as a first testing fluid into the interior of said housing at a first location adjacent to said test sample whereby said test sample and said contact element are subjected to a testing fluid environment containing atomic oxygen while in the active state; and (f) means for evacuating gases from the interior of said housing at a second location when in the closed state concurrently with the introduction of said atomic oxygen in order to maintain atomic oxygen in the testing fluid environment, the first and second locations being oriented with respect to said sample station such that said atomic oxygen flows across said test sample and said contact element.

12. Apparatus according to claim 11 further comprising a pressure sensor operative to sense gas pressure in the interior of said housing and including process control means for monitoring and controlling said gas pressure.

13. Apparatus according to claim 11 further comprising a temperature sensor operative to sense the temperature of said atomic oxygen and process control means for monitoring said temperature.

14. Apparatus according to claim 13 further comprising means for regulating the temperature of said atomic oxygen, said process control means operative to control said means for regulating said temperature.

15. Apparatus according to claim 11 further comprising at least one source of a second testing fluid, means for introducing said second testing fluid into the interior of said housing at a third location when in the closed state independently of said atomic oxygen so that said atomic oxygen and said second testing fluid define a testing fluid environment, the third location being oriented with respect to the first and second locations and said sample station such that the testing fluid environment flows across said test sample and said contact element, means for monitoring the composition of said testing fluid environment, and process control means for independently adjusting the relative rate of introduction of said atomic oxygen and said second testing fluid whereby a selected ratio of atomic oxygen to said second testing fluid is maintained.

16. Apparatus according to claim 11 wherein said means for introducing atomic oxygen includes a source of molecular oxygen in fluid communication with an asher plasma generator, said asher plasma generator having an antenna disposed in the interior of said housing and in fluid communication with said source of molecular oxygen whereby molecular oxygen is disposed at said antenna into atomic oxygen.

17. An apparatus for testing a test sample in the presence of a selected testing fluid environment, comprising:
  (a) a housing having an interior and comprising a bottom wall, a surrounding sidewall and a removable top wall whereby said housing may be opened to allow access to the interior thereof, said top wall being securable to said housing whereby said housing may be closed to isolate the interior thereof;
  (b) a carriage disposed in the interior of said housing, said carriage mounted for reciprocal movement with respect to said bottom wall;
  (c) a first drive system including a first ferromagnetic coupling mounted through said sidewall, a first motor disposed exteriorly of said housing and a first drive assembly disposed interiorly of said housing and interconnected with said carriage, said first motor drivably interconnected to said first drive assembly by way of said first ferromagnetic coupling whereby said first motor may linearly move said carriage reciprocally at a selected rate between first and second limits;
  (d) a turntable disposed in the interior of said housing and spaced at a selected first distance from said carriage along said bottom wall, said turntable adapted to support a test sample thereon to define a first sample station for rotational movement with respect to said bottom wall;
  (e) a second drive system including a second ferromagnetic coupling mounted through said bottom wall, a second motor disposed exteriorly of said housing a second drive assembly disposed interiorly of said housing and interconnected with said turntable, said second motor drivably interconnected to said second drive assembly by way of said second ferromagnetic coupling whereby said second motor may rotatably drive said turntable at a selected rate;
  (f) a support arm having a first arm end mounted to said carriage for common movement therewith and a second arm end opposite said first arm end, said support arm positionable in a first orientation whereby said second arm end is adjacent to said turntable;
  (g) a contact element disposed on said second arm end and operative in an active state to contact a surface of said test sample with a contact force of selected magnitude when said test sample is supported on said sample station, said carriage operative to reciprocally move said contact element radially with respect to said turntable when reciprocally driven by said first drive system; and
  (h) means for introducing a testing fluid into the interior of said housing when in a closed state whereby said test sample and said contract element are subjected to a selected testing fluid environment when in the active state.

18. Apparatus according to claim 17 further comprising first and second sensors adapted to sense the position of said carriage respectively at said first and second limits, said first and second sensors being operative to cause the linear motion of said carriage to reverse direction when said carriage respectively reaches said first and second limits.

19. Apparatus according to claim 18 wherein the relative position of said first and second sensor is adjustable whereby the distance of travel of said carriage may be varied.

20. Apparatus according to claim 18 wherein said first and second sensors are optical interrupters.

21. Apparatus according to claim 17 wherein said first motor is a variable speed motor whereby the rate of travel of said carriage may be varied.

22. Apparatus according to claim 17 wherein said second motor is a variable speed motor whereby the rate of rotation of said turntable may be varied.

23. Apparatus according to claim 17 further comprising a strain gauge associated with said support arm and adapted to measure strain on said contact element.

24. Apparatus according to claim 17 further comprising a stationary block disposed in the interior of said housing and spaced from said turntable and spaced at a selected second distance from said carriage along said bottom wall equivalent to said first distance, said stationary block adapted to support said test sample thereon to define a second sample station, said support arm positionable in a second orientation with respect to said carriage wherein said second arm end is proximate to said stationary block, said support arm being demountable from said carriage whereby said support arm may be interchangeably secured in a selected one of said first and second orientations.

25. Apparatus according to claim 17 further comprising means for varying the magnitude of said contact force.

26. Apparatus according to claim 17 further comprising cuing means for cuing said support arm whereby said contact element may be lowered onto and raised off of said test sample when said sample is place on said turntable.

27. Apparatus according to claim 17 further comprising a vacuum pump in fluid communication with the interior of said housing and operative to evacuate the interior when said housing is closed.

28. A method of testing a test sample of material in a controlled environment different from an ambient environment comprising the steps of:
  (a) providing a closed environment housing having an interior that may be isolated from the ambient environment and which has disposed therein a sample support station adapted to support a test sample thereon;
  (b) placing the test sample on said sample support station;
  (c) contacting a surface of said test sample with a contact element at a selected contact force when said test sample is supported on said sample support station;
  (d) isolating the interior of said closed environment housing from the ambient environment;
  (e) introducing a testing fluid into the interior of said housing at a first location;
  (f) removing the testing fluid from the interior of said housing concurrently with the introduction of said testing fluid whereby said testing fluid flows across said test sample and said contact element so that said test sample and said contact element are subjected to a selected testing fluid environment;
  (g) reciprocally moving said contact element relative to said surface at a selected rate when said contact element is in contact therewith whereby said surface is subjected to wear along a wear path; and
  (h) measuring an amount of wear occurring along the wear path after a selected interval of time.

29. A method according to claim 28 further comprising the step of evacuating the interior of said closed housing to a pressure below ambient pressure after isolation and prior to introduction of the testing fluid.

30. A method according to claim 28 further comprising the step of maintaining said testing fluid environment at a selected temperature.

31. A method according to claim 28 further comprising the step of maintaining said testing fluid environment at a selected pressure.

32. A method according to claim 28 further comprising the step of rotating said test sample contemporaneously with the step of reciprocally moving said contact element.

33. A method according to claim 28 wherein said testing fluid comprises atomic oxygen.

34. A method according to claim 33 further comprising the step of producing said atomic oxygen from molecular oxygen at a location proximate to said sample support station.

35. A method according to claim 28 further comprising the step of providing a plurality of different testing fluids and the step of introducing said testing fluids into the interior of said closed housing and the step of monitoring the testing fluid environment to maintain said testing fluids at a desired relative ratio.

* * * * *